(12) United States Patent
Guirguis et al.

(10) Patent No.: US 6,531,317 B2
(45) Date of Patent: Mar. 11, 2003

(54) CYTOLOGICAL AND HISTOLOGICAL FIXATURE COMPOSITION AND METHODS OF USE

(75) Inventors: Raouf A. Guirguis, Vienna, VA (US); Mariamena El-Amin, Bethesda, MD (US)

(73) Assignee: LaMina, Inc., Arlington, VA (US)

( * ) Notice: Subject to any disclaimer, the term of this patent is extended or adjusted under 35 U.S.C. 154(b) by 0 days.

(21) Appl. No.: 09/741,861

(22) Filed: Dec. 22, 2000

(65) Prior Publication Data

US 2002/0094577 A1 Jul. 18, 2002

Related U.S. Application Data

(63) Continuation of application No. PCT/US99/14783, filed on Jun. 30, 1999.
(60) Provisional application No. 60/091,174, filed on Jun. 30, 1998.

(51) Int. Cl.[7] .................................................. G01N 1/30
(52) U.S. Cl. ........................ 436/18; 436/8; 252/408.1; 252/380; 252/397; 435/40.5; 435/40.51; 435/40.52
(58) Field of Search ................................ 436/8, 17, 18; 252/408.1, 380, 397; 435/40.5, 40.51, 40.52; 424/75

(56) References Cited

U.S. PATENT DOCUMENTS

| | | | | |
|---|---|---|---|---|
| 4,493,821 A | * | 1/1985 | Harrison | 424/3 |
| 4,978,624 A | * | 12/1990 | Cremins et al. | 436/17 |
| 5,188,935 A | * | 2/1993 | Leif et al. | 435/7.24 |
| 5,196,182 A | * | 3/1993 | Ryan | 424/3 |
| 5,422,277 A | * | 6/1995 | Connelly et al. | 436/10 |
| 5,639,630 A | * | 6/1997 | Malin et al. | 435/28 |
| 5,976,829 A | * | 11/1999 | Birnboim | 435/40.5 |
| 6,026,174 A | * | 2/2000 | Palcic et al. | 382/133 |
| 6,207,408 B1 | * | 3/2001 | Essenfeld et al. | 435/40.5 |

OTHER PUBLICATIONS

Boyles et al./ *The Journal of Cell Biology*, vol. 101, pp. 1463–1472 Oct. 1985*

* cited by examiner

Primary Examiner—Maureen M. Wallenhorst
(74) Attorney, Agent, or Firm—Foley & Lardner

(57) ABSTRACT

The present invention is directed to a fixative composition, the use of the fixative composition in preparing cytological or histological specimens, and a method of preparing particulate matter, such as cytology, hematology and microbiology specimens, for examination by collecting the particulate matter in a uniform layer, preferably a monolayer, and fixing the particles in a composition according to the present invention. The cytological, hematological, microbiological and histological fixative composition of the present invention contains an aldehyde crosslinker, a polyol and a detergent. The method of the present invention for preserving the particulate or histological specimen uses the fixative composition containing an aldehyde crosslinker, a polyol and a detergent.

17 Claims, No Drawings

CYTOLOGICAL AND HISTOLOGICAL FIXATURE COMPOSITION AND METHODS OF USE

This application is a continuation of PCT/US99/14783, filed Jun. 30, 1999, which claims priority of U.S. provisional application Ser. No. 60/091,174, filed Jun. 30, 1998.

TECHNICAL FIELD OF THE INVENTION

The present invention is directed to a fixative composition, the use of the fixative composition in cytological procedures, and a method of preparing particulate matter, such as cytology, hematology and microbiology specimens, for cytological or histological examination comprising collecting a particulate matter sample in a uniform layer, preferably a monolayer, and fixing the particles in a composition according to the present invention.

BACKGROUND OF THE INVENTION

In a wide variety of technologies, the ability and/or facility in separating matter, typically particulate matter, from a fluid is a critical component in the ability to test for the presence of substances in the fluid. Too often, interference associated with sample preparation obscures the target cells to such a degree that the process is not sufficiently reliable, or too costly. Such issues apply to many other fields which involve detection and/or diagnosis, including environmental testing, radiation research, cancer screening, cytological examination, microbiological testing, and hazardous waste contamination, to name just a few.

All that is required for a cytological examination of a sample is that a sample of cells be obtained from the patient, which can typically be performed by any one of the number of well known techniques including any of the following techniques: direct scrapings, scraping or swabbing an area (as in the case of cervical samples), brushings, collection and concentration of a fluid specimen with a standard preparatory centrifuge, fine needle aspiration or any other known method, or by collecting body fluids, such as those obtained from the chest cavity, bladder, or spinal canal. In a conventional manual cytological examination, the cells in the fluid are then transferred onto a glass slide for viewing. In a conventional automated cytological examination, a filter assembly is placed in the liquid suspension and the filter assembly both disperses the cells and captures the cell on the filter, and the filter is removed and placed in contact with a microscope slide. In all of these endeavors, a limiting factor in the sample preparation protocol is adequately separating solid matter from its fluid carrier (e.g., a variety of fluids, such as physiological, biological and environmental), and in easily and efficiently collecting and concentration the solid matter in a form readily accessible to microscopic examination.

Another limiting factor in optimally preparing the particulate matter for microscopic examination involves the solution and/or solutions for fixing the particulate matter to a microscope slide or the like.

A number of urine or other biological fluid specimen containers have been developed to allow liquid biological specimens to be tested without removing the lid of the urine or biological fluid container. None of the prior art solves the problem of transferring cells in a uniform layer to a slide for examination while at the same time preserving the fluid from which the cells were taken.

Currently, body fluid samples are collected for cytological examinations using special containers. These containers usually contain a preservative solution for preserving the cytology specimen during shipment from the collection site to the cytology laboratory. Furthermore, cytology specimens collected from the body cavities using a swab, smear, flush or brush are also preserved in special containers with fixatives (e.g., alcohol or acetone fixatives) prior to transferring cells onto the slide or membrane for staining or examination.

Diagnostic microbiology and/or cytology, particularly in the area of clinical pathology, bases diagnoses on a microscopic examination of cells and other microscopic analyses. The accuracy of the diagnosis and the preparation of optimally interpretable specimens typically depends upon adequate sample preparation. New methodologies such as immunocytochemistry and image analysis require preparations that are reproducible, fast, biohazard-free and inexpensive. Different cell preparation techniques of the present invention address the issues of non-uniform cell densities, uneven cell distribution and air drying artifact. These preparations have resulted in an even distribution of cells that have superior morphology, which has improved light microscopic visualization and has allowed for the use of image cytometry instruments.

The solid matter preparation techniques of the present invention address the issues of non-uniform matter densities, uneven matter distribution, and sample loss due to the number of steps involved in the sample preparation. The preparations of the present invention result in an even distribution of solids that have superior morphology, improved visualization, and are readily positioned and available for light absorbence analysis without the need to further manipulate or prepare the sample.

Properly fixing (i.e., preserving) cytologic material such as cells, cell aggregates and small tissue fragments derived from cytologic collections of human or animal tissue is a prerequisite to the accurate diagnosis of disease, especially cancer. Cytologic material must be fixed as soon as possible after obtaining the material to prevent cell distortion.

Cytologic specimens, which constitute the examinable form of the cytologic material, may be prepared by well-understood smear or fluid techniques. Because there may be a considerable lapse of time before these specimens are further processed by staining, applying a cover slip, and so forth, however, it is important to apply a fixative to the cytologic material as a means of preserving and fixing the cells.

Air-dried and tetrachrome-dye stained cytologic specimens, although popular abroad, are not generally used in the United States. Rather, wet fixation, either by the immersion of slides into an alcohol solution, by saturation of slides with a spray fixative or by directly discharging cytologic material into an alcohol solution, is a known method of cell fixation. Cell fixation is a prerequisite for interpretable Papanicolaou, Hematoxylin and Eosin or other stained cytologic specimen slides.

Generally, alcohol solutions, with or without other additives such as polyethylene glycol, ranging from 50% to 95% (v/v: methanol, ethanol, isopropanol) are known solutions for use in wet fixation. When alcohol solutions greater than 50% (v/v) are used for collecting and fixing fluids high in protein, however, a protein sediment forms which subsequently hardens. Protein sedimentation makes the fixed cytologic material difficult to transfer to glass slides for examination, regardless of whether the transfer is done by direct application to the glass slide, by cytofiltration through a small pore filter, or by cytocentrifugtion onto glass slides coated with an adhesive such as chrome aluminum gelatin.

For over a century, tissue fixative compositions used to preserve and prepare tissue for analytical evaluation have been based on formaldehyde. The standard composition employed for tissue preservation and the preparation of thin-cut tissue for microscopic examination is Formalin. Formalin is a 3 to 10 percent solution of formaldehyde in water, usually containing about 15 percent methyl alcohol. Alcohol improves the preservative properties of the solution. Despite numerous disadvantages, most notably high toxicity and irritant properties, Formalin remains the fixative of choice in typical laboratory applications owing to its rapid reaction with exposed tissue surfaces and consequent maximized cellular preservation. Methanol may adversely affect the texture of the tissue, rendering it too brittle or, more usually, too soft for ease in cutting for slide preparation. It also may produce pigmented artifacts or impurities which interfere with staining. Formalin containing methanol nevertheless provides preserved tissue which can be satisfactorily sectioned and stained for microscopic examination.

Histologists have long endeavored to develop effective immunohistochemical fixatives and morphologic fixatives. Moreover it is desirable to preserve morphologic detail preserve tissue antigens to permit immunohistochemical detection and localization of antigens in tissue.

Such fixatives render protein insoluble. For example, formaldehyde may be used as a crosslinking agent forming covalent bonds between the aldehyde groups and specific amino acids to stabilize protein structure and transform the cell cytoplasm into a gel which prohibits movement of autolytic enzymes. Alternately, alcohol may be used as a fixative to precipitate protein through denaturation.

Preferably, a fixative should retard autolysis and putrefaction and preserve morphologic detail and antigenicity. Unfortunately, an effective morphologic fixative is not necessarily an effective immunohistochemical fixative.

SUMMARY OF THE INVENTION

The present invention relates to a fixative composition and method for preserving a cytological or histological specimen. The compositions and methods of the present invention are particularly suitable for separating matter from biological, physiological, and environmental fluids and presenting the particulate matter in an improved manner for examination.

The present invention is directed to a cytological and histological fixative containing an aldehyde crosslinker, a polyol and a detergent. The aldehyde of the composition is typically a $C_1$–$C_6$ alkanal or a $C_1$–$C_8$ alkylene dialdehyde, such as glutaraldehyde, formaldehyde, paraformaldehyde, acetaldehyde, propionaldehyde, or butyraldehyde. The polyol of the composition typically may be ethylene glycol, propylene glycol, glycerol, sorbitol, and mannitol. The preferred detergent is a non-ionic detergent, such as Triton X-100, Nonidet P40, Igepal Ca-630, Tween® 85, Tween® 80, or Tween®65.

The fixative composition of the present invention may further contain any of the following: a buffer that maintains the solution at a pH between about 4 and about 7, such as Tris or phosphate buffered saline; a nucleoprotein precipitator, such as acetic acid; a hemolytic agent, such as acetic acid; an osmolarity maintainer, such as dextrose or sodium chloride; a solvent such as ethanol, isopropanol, methanol and water; a ketone, such as acetone or methyl ethyl ketone; a cell coating substance, such as polyethylene glycol (PEG) or Carbowax and a mucolytic agent, such as dithiothreitol (DTT) or acetylcysteine.

The fixative composition of the present invention preferably contains an aldehyde concentration of about 0.2 to 4.0%, a glycerol concentration of about 0.5 to about 2.0% and a detergent concentration of about 0.01 to 0.05%. The composition of the present invention may also include alcohol at a concentration of about 35 to about 45%, acetone at a concentration of about 2.0 to 3.0%, polyethylene glycol at a concentration of about 1.0 to 3.0% and/or a buffer.

The present invention is also directed to methods of preserving a cytological or histological specimen by fixing the specimen with an effective amount of the composition of the present invention.

The present invention is also directed to a tissue fixative composition for use in histopathological applications which rapidly penetrates tissue surfaces for maximum cellular preservation, leaves minimal pigmented artifacts, and permits accurate staining. The present invention is also directed to providing a cytologic and histologic fixative formulation that fixes and preserves cells, cell aggregates and small tissue fragments in a liquid suspension.

The present invention is also directed to providing a fixative formulation that retains tissue samples which are incidentally collected along with cytologic material for further histological processing.

The present invention is also directed to providing a fixative formulation that allows shipments of the liquid suspension of cells, cell aggregates and tissue fragments under conditions typically encountered in postal carriage, permitting remote users without available cytologists, cytotechnologists, physicians or other personnel experienced in the preparation of cytologic samples to fix a cytologic specimen for later processing, and whereby technically satisfactory cytologic sample slides may be produced therewith.

The invention in another aspect concerns a method of preparing tissue for cutting, staining and/or microscopic evaluation wherein the specimen tissue prior to dehydration is subjected to preservation with a storage stable tissue fixative solution of the present invention.

A unique cytologic and histologic fixative formulation and methods for using that formulation are disclosed. The formulation fixes and preserves individual cells, aggregates of cells and small fragments of tissue in a liquid suspension; minimizes protein precipitation in the liquid suspension; selectively eliminates or reduces red blood cell contamination of cytologic material and cytologic specimen slides; retains tissue samples that are incidentally collected along with cytologic material for further histologic processing; and allows shipment of cytologic material under conditions typically encountered in postal carriage, permitting remote users without available cytologists, cytechnologists or other personnel experienced in the preparation of cytologic samples to have technically satisfactory cytologic sample slides.

DETAILED DESCRIPTION OF THE INVENTION

A composition according to the invention includes one or more solvents, preferably an alkanol, between about 35% and about 45% by volume; ketone, between about 2% and about 3% by volume; a diluent, preferably a diol or triol, from about 1% to about 3% by volume; a crosslinker, preferably an aldehyde, from about 0.2% to about 4% by volume; glycerol, from about 0.5% to about 2% by volume; one or more detergents and/or dispersing agents, preferably non-ionic, from about 0.01% to about 0.05% by volume; and a buffer, from about 45 to about 65% by volume. In a preferred embodiment of the invention, the pH of the composition is between about 4 and about 7.

The present invention also includes the use of a fixative composition as described above in cytological and/or histological procedures. The fixative composition of the present invention is particularly suitable for use with a particulate matter collection device selected from that disclosed in U.S. Pat. No. 5,471,994; U.S. Pat. No. 5,301,685; U.S. Pat. No. 6,106,483, U.S. Ser. No. 08/963,873 filed Nov. 4, 1997, U.S. Pat. No. 6,149,871, U.S. Pat. No. 6,309,362, WO 99/07823; U.S. Ser. No. 09/050,010 filed Mar.30, 1998; WO 99/10723; U.S. Pat. No. 6,296,764 and WO 99/23468.

The present invention also includes a method of preparing cytological or histological specimens, and a method of preparing particulate matter, such as cytology, hematology and microbiology specimens, for examination by collecting the particulate matter by collecting the particulate matter in a uniform layer, preferably a monolayer, and fixing the particles in a composition according to the present invention.

Table 1 summarizes the range and preferred concentrations of the components of a fixative formulation according to the present invention.

| Component | range (by volume, %) | preferred (by volume, %) | example |
| --- | --- | --- | --- |
| solvent | 35–45 | 37–42 | alcohol |
| ketone | 2.0–3.0 | 2.1–2.4 | acetone |
| cell coating | 1.0–3.0 | 1.6–1.9 | PEG |
| polyol | 0.5–2.0 | 0.8–1.2 | glycerol |
| crosslinker | 0.2–4.0 | 0.6–0.8 | Formaldehyde glutaraldehyde |
| detergent | 0.01–0.0 | 0.02 | Nonidet P40 |
| buffer | 45–65 | 50–55 | Tris |
| Mucolytic agent | 0.1–1.0 (grams %) | 0.2–0.5 (grams %) | dithiothreitol acetylcysteine |

An exemplary formulation of a composition according to the invention comprises about 40% by volume of alcohol (e.g., isopropanol and methanol), about 2–3% acetone, about 1.0–3.0% polyethylene glycol; about 2% by volume of formaldehyde (e.g., commercially available as formalin, a 3–37% v/v solution in water, sometimes including methyl alcohol); and about 58% by volume of buffer (e.g., Tris). The preferred pH of this formulation is about 5.0±0.5. Another useful formulation is shown in Example 1.

A composition according to the invention includes one or more solvents to penetrate the tissue or cells, dehydrate the cells, and/or inhibit bacterial and vital activity. In a preferred embodiment of the invention, the solvent is a mixture of alkanols, which penetrate slowly, and when combined with other reagents, fixes the sample rapidly. It denatures protein by precipitation, precipitates glycogen, and dissolves fats and lipids. The alkanol can be any of thee well known alcohols having one to four carbons, e.g., methanol, ethanol, n-propanol, isopropanol, n-butanol, and various branched butanols. The most preferred solvent is a mixture of methanol and isopropanol, typically about 30% and about 10% by volume, respectively.

The ketone is a fixative with similar action to that of alcohol, except that glycogen is not well preserved. The ketone acts as a fixative and additionally enables the overall composition to penetrate the cells. The preferred ketone is acetone.

The coating over the specimen helps protect the cells or tissue from the effects of drying. The preferred coating is polyethylene glycol (PEG) or Carbowax. The coating is important to prevent shrinkage of the cells and to retain nuclear detail.

The polyol, such as glycerol, prevents the drying of cells during sample processing. Cells that have been kept in fixative solution for an extended time typically become rigid due to the fixing process and are less able to spread on the slide. The polyol helps the cells to flatten on the slide. The preferred polyol is ethylene glycol, propylene glycol, glycerol, sorbitol, and mannitol, most preferably glycerol.

The crosslinker reacts with protein end-groups to crosslink molecules and produces an insoluble product. Protein groups involved include amino, imino, and amido, peptide, hydroxyl, carboxyl and sulfhydryl. Methylene bridges are also commonly formed between similar groups such as $NH_2$ and NH but are thought to be reversible by washing in water. Some crosslinkers such as formaldehyde are an antiseptic.

The preferred crosslinkers are aldehydes, such as a $C_1$–$C_6$ alkanal or a $C_1$–$C_8$ alkylene dialdehyde. The preferred aldehyde crosslinker is glutaraldehyde, formaldehyde, paraformaldehyde, acetaldehyde, propionaldehyde, or butyraldehyde, most preferably formaldehyde.

The detergent, such as a non-ionic detergent, is used as a dispersing agent and for solubilizing proteins and membrane components to diminish cellular aggregation. The preferred detergents are Triton X-100 (a polyethylene glycol; α-[4-(1,1,3,3- tetramethylbutyl)phenyl]- ω-hydroxy-poly(oxy-1, 2-ethanediyl)), Nonidet P40 (a polyethylene glycol; α-[(1, 1,3,3,-tetramethylbutyl)phenyl]- ω-hydroxy-poly(oxy-1,2-ethanediyl)) Igepal Ca-630 (a polyethylene glycol; α-[(1,1, 3,3,-tetramethylbutyl)phenyl]- ω-hydroxy-poly(oxy-1,2-ethanediyl)), TWEEN® 85(an ethoxylated sorbitan trioleate; sorbitan, tri-(9Z)-9-octadecenoate, poly(oxy-1,2-ethanediyl) derivative), TWEEN® 80 (an ethoxylated sorbitan monoleate; sorbitan, tri-(9Z)-9-octadecenoate, poly (oxy-1,2-ethanediyl) derivative), and TWEEN®65(an ethoxylated sorbitan tristearate; sorbitan, tri-(9Z)-9-octadecenoate, poly(oxy-1,2-ethanediyl) derivative).

The buffer maintains the solution at a pH between about 4 and about 7, and provides a medium for transportation. The preferred buffer is Tris, a well known buffer. In accordance with the present invention, the buffer may also include a fixative that precipitates nucleoproteins and one or more osmolarity maintainers. The preferred nucleoprotein precipitator is acetic acid, which acts also as a hemolytic agent to lyse red blood cells. Typically, the acetic acid is present in a range from about 0.2% to about 2.0% by volume. With the increase in concentration of acetic acid in the buffer, hemolysis occurs. The preferred osmolarity maintainers are dextrose, typically in a range from about 0.1% to about 0.2% by weight, and sodium chloride, typically in a range from about 0.7% to about 0.8% by weight.

A mucolytic agent is included in the fixative composition of the present invention for use in preparing a particulate monolayer from mucoid specimens such as: sputum, bronchial alveolar washings and lavages, gastric washings and lavages. Examples of mucolytic agents to be used in the present invention include: dithiothreitol (DTT), acetylcysteine, bromhexine, carbocysteine, domiodol, letosteine, lysozyme, mecysteine hydrochloride, mesna, sobrerol, stepronin, tiopronin, and Tyloxapol. The preferred mucolytic agent is dithiothreitol (DTT) or acetylcysteine, typically employed in a range of 0.1–1.0% by gram. The preferred range is 0.2–0.5%. DTT is a water-soluble reagent ideally suited for protecting sulfhydryl groups. DTT easily permeates cell membranes and, with its low redox potential, prevents oxidation of proteins. DTT also maintains monothiols in the reduced state and reduces disulfides quantitatively.

In the preferred embodiment, the active fixative ingredients described may be dissolved in a suitable solvent such as distilled water, and this solution can then be used as a fixative agent in a number of ways as would be obvious to one skilled in the art. For example, the fixative solution can be used to preserve samples of tissue that are being shipped or carried to an examination site. In this process, small vials or jars that have liquid tight seals are filled with the reagent of the invention, and tissue samples are placed in the reagent-containing vial to preserve the samples until they reach an area where further processing can occur. Water or other diluent is also used in an amount of about 80 to about 0 percent by volume. Any suitable diluent that does not change the important chemical and physical characteristics of the formulation may be used.

Tissues prepared for study using the fixative of the invention can be prepared for histological study in any known conventional manner, such as through the use of paraffin, sectioning equipment, staining, mounting on slides, or other common steps utilized prior to microscopic or other examination. The present invention thus provides a safe, convenient and effective fixative solution which can be utilized in the many known histological procedures that employ such solutions.

The present invention also includes devices and methods for collecting fluids, such as biological, physiological, or environmental fluids, removing the desired matter from the fluid, without centrifugation, and diagnosing and testing the matter. In a preferred embodiment of the invention, particulate matter is collected on a collection site. In a most preferred embodiment of the invention, the particulate matter is collected in a monolayer, typically in a pre-determined spatial arrangement.

The present invention also includes a fixative composition as described above, used with an apparatus and method that includes dispersing particulate matter in the sample, preferably by rotating the sample container around a fixed agitator or the like.

The present invention is also a fixative composition as described above used with an improved device for collecting and processing a fluid, typically a biological fluid, the device including a particulate matter collection chamber having one or more of the following: a collection site; a membrane for separating particulate matter from a liquid; a porous support; a porous support with at least one throughgoing bore, preferably a bore positioned near the circumference of the porous support, said bore providing additional surface tension so that a filter membrane is retained on the porous support when the housing is opened to expose the membrane for further processing; a porous arrangement that establishes at least two fluid flow paths through the collection chamber; a porous arrangement seat that configures the collected particulate matter in a predetermined pattern; a collection chamber having a concentric channel; a channel having one or more resilient members; a chamber seat having one or more resilient members; a chamber seat or base having posts; a chamber seat having one or more pre-determined surface modifications; a seat having one or more elements that promote a pre-determined spatial arrangement of particulate matter on the collection site; and structures that enhance the fluid flow through the chamber.

An apparatus for use with the fixative composition of the present invention may also include structures that are configured for and/or are adapted to mix the specimen collected in the collection chamber. Exemplary structures include but are not limited to a collection chamber having a rotatable cover, or a portion of the cover that rotates; a cover or cover portion that is moveable in relation to the collection container; and a tube or the like that extends into the collection container, said tube including one or more elements that mix the specimen. The cover may also include a portion that fittingly engages a portion of the cover in a liquid tight seal. The cover may also include a portion that fittingly engages a portion of the cover in a liquid-tight but not fluid-tight seal.

The compositions, devices, and methods of the present invention may be configured into or used with a hand-held manual system or structure, a partially automated system or structure, or a fully automated system or structure.

The present invention also includes preparing a sample for microscopic examination by processing a sample using a device according to the invention, and collecting particulate matter on a collection site in the device.

The present invention also includes a method for analyzing matter comprising collecting a sample in a collection container, collecting matter on a collection element, and transferring the matter collected on the collection element to a microscope slide or the like. Preferably, both collecting steps occur within the same apparatus.

In a preferred embodiment of the invention, a specimen cup includes a chamber for collecting a liquid specimen, and in fluid communication with the chamber, a particulate matter separation chamber or module for separating particulate matter in the fluid and collecting the separated particulate matter in a collection zone. In a most preferred embodiment of the invention, the separated particulate matter is collected in a monolayer on the collection zone. A preferred embodiment of the invention also includes a hollow tube in fluid communication with the particulate matter separation chamber. More preferably, the hollow tube includes means for mixing the specimen and/or dispersing the particulate matter in the specimen. Exemplary means include but are not limited to an agitator, fins, brush, swab, broom, spatula, or the like. A preferred embodiment of the invention includes a tube having a brush. An exemplary brush is disclosed in U.S. Pat. No. 4,759,376 incorporated herein by reference.

As used herein, "sample" refers to any fluid in combination with solid matter, such as particulate matter, and from which it may be desirable to collect the particulate component from the sample for the purpose of establishing its identity or presence in the sample. Typically, the fluid component of the sample will be a liquid. However, the fluid may also be air or gas. As an example, it may be desirable to determine the presence of cancer cells or certain proteins in the biological fluid, such as urine. In another example, it may be desirable to evaluate the nature of contaminants, such as molecular contaminants, in ultra-pure water used in the electronics industry. Other exemplary fluids include but are not limited to body fluids, such as blood, spinal fluid, or amniotic fluid; bronchial lavage; sputum; fine needle aspirates; ground water; industrial processing fluids; and electronic or medical dialysis fluids, to identify just a few. It is intended that the invention should not be limited by the type of fluid being processed.

As used herein, particulate matter refers to any substance in a fluid which is capable of collection and evaluation, preferably by cytological, hematological or microbiological examination. Exemplary particulate matter includes, but is not limited to cells or cell fragments, bacteria, blood components, proteins, molecules, polymers, rubbers, stabilizers, antioxidants, accelerators, silicones, alkyds, thiokols, paraffins, thermoplastics, bacteria, pesticides, and herbicides. Specific exemplary polymeric matter include, but is not limited to polyethylene, polypropylene, polyisobutylene, polyacrylonitrile, polyethylene glycol, polyvinylchloride, polystyrene, polysulfide, polymethylmethacrylates, polyethyleneterephthalates, ethyl cellulose, nitrocellulose, polyurethane, and nylon. A specific exemplary environmental contaminant is bisphenol A. Specific exemplary biological matter includes cancer cells, including distinguishing between metastatic and normal cancer cells; proteins, nucleic acids, antibodies, or the like. It is intended that the invention should not be limited by the type of matter being processed.

While a cytology collection apparatus and/or fixative composition according to the invention can be used for any biological fluid, it is particularly useful for preparing testing samples from urine and its associated cells for Pap smears. The most widely used stain for visualization of cellular changes in cytology is the Papanicolaou staining procedure. This stain, which is used for both gynecologic and non-gynecologic applications, is basically composed of blue nuclear and orange, red and green cytoplasmic counter-stains. The nuclear stain demonstrates the chromatic patterns associated with normal and abnormal cells, while the cytoplasmic stains help to indicate cell origin. The success of this procedure can be attributed to the ability to observe a number of factors, including definition of nuclear detail and cell differentiation. This staining procedure also results in a multicolor preparation that is very pleasing to the eye, possibly reducing eye strain.

It is intended that the invention should not be limited by the type of matter being processed. In a most preferred embodiment of the invention, the fluid is urine and particulate matter is a cell.

The composition and method of the present invention also permits isolation and collection of fresh cells and/or microorganisms from biological fluids to perform DNA probe and chromosomal analysis once the cells are hemolyzed by the proper buffer.

As used herein, adapted for communication, communicating, or similar terms refer to any means, structures, or methods for establishing fluid flow through the system, as are well known by practitioners in the art. Exemplary structures are shown in the Figures. For example, a conduit may have a connector adapted to receive or connect to a mated connector on another conduit. As used herein, connector refers to any structure used to form a joint or to join itself to another piece. These connectors or connections establish a fluid flow path through various elements of the apparatus, assembly, or system. Typical connections include but are not limited to mating connections, such as Luer-type, screw-type, friction-type, or connectors that are bonded together.

As used herein, "adapted for engaging", "engagement", "engaging", or similar terms refers to complementary structures that may align, mesh, mate or rest near, against, or within each other. Exemplary structures include the connectors described above.

The present invention also includes a the method for removing particulate matter from a fluid, and for transferring particulate matter, such as cells or bacterial or a blood sample, to a microscope slide. In contrast to currently available methods, the use of membrane filtration provides a method of depositing cells evenly over a microscope slide with minimal overlap. This allows for clear observation and optimal diagnostic accuracy.

The porous medium may then be pressed against a microscope slide to allow particulate matter collection on the collection site to be transferred as they were collected onto the slide. This allows a cytological examination to be performed on the cells by the practitioner without the interference of the pores in the membrane or delay due to processing requirements.

Since cellular detail is dependent on fixation, it is preferred that cells be fixed immediately after being deposited on the slide. Too long a delay between preparation and fixation may expose the cells to drying, which may be detrimental to the cellular structure. Moreover, air drying artifacts can adversely affect the subsequent staining results. An exception is when the cells are stained with Wright-Giemsa, where air drying is used as the fixation step.

In an another embodiment of the present invention, the monolayer of cells may be fixed directly on the collection site. This may be carried out by first depositing a monolayer of cells on the collection site of the cytology collection apparatus as described above and subsequently passing a solution containing a fixative, such as alcohol or acetone, through the cytology collection apparatus.

It should be noted that various types of porous arrangements can be used interchangeably with that of the present embodiment. While a polycarbonate membrane is especially suitable for use in the cytology collection apparatus of the present invention, other porous membranes are also suitable. Exemplary porous membranes are well known in the art, and are disclosed in U.S. Pat. Nos. 5,471,994 and 5,301,685, both hereby incorporated by reference.

Included within the scope of the present invention is producing a single slide from a patient sample, producing multiple slides from a single patient sample, or producing multiple slides from multiple patient samples. It is intended that a patient sample may be processed in a single shot, batch, or continuous manner. Additional slides for other stain applications can be easily prepared. Human papilloma virus testing, for example, by newer methods such as immunocytochemistry or in-situ hybridization can be performed on the additional slides. As oncogene products or other immunocytochemical tests are developed, more slides may be necessary. The different fixations that these tests may need can easily be incorporated into the procedure since the preparation does not require the slides to be fixed in only one way.

This same slide preparation procedure can be used for virtually all forms of cytology. Furthermore, the use of completely contained disposable components addresses biohazard concerns. Ultimately, the enhanced presentation of cells, yielding improved cytologic interpretation, may expand the role of cytology by providing more consistent and reliable patient diagnosis.

The most widely used stain for visualization of cellular changes in cytology is the Papanicolaou staining procedure. This stain, which is used for both gynecologic and non-gynecologic applications, is basically composed of blue nuclear and orange, red and green cytoplasmic counter-stains. The nuclear stain demonstrates the chromatic patterns associated with normal and abnormal cells, while the cytoplasmic stains help to indicate cell origin. The success of this procedure can be attributed to the ability to observe a number of factors, including definition of nuclear detail and cell differentiation. This staining procedure also results in a multicolor preparation that is aesthetic, possibly reducing eye strain.

The compositions and methods of the present invention are particularly suited for preparing particulate matter, such as cytology, hematology and microbiology specimens, as well as for preserving histology specimens.

EXAMPLES

Example 1

Fixative Formulation

The following fixative composition was produced: 40% alcohol (methanol and isopropanol); 2.2% acetone; 1.8% polyethylene glycol (PEG); 0.7% formaldehyde; 1% glycerol; 0.02% Nonidet P40; and 54% Tris Buffer (pH 7.4–7.8). All amounts are approximate percentages by volume.

The present invention also includes the use of a fixative composition as described above in cytological and/or histological procedures. The fixative composition of the present invention is particularly suitable for use with a particulate matter collection device selected from that disclosed in U.S. Pat. No. 5,471,994; U.S. Pat. No. 5,301,685; U.S. Pat. No. 6,106,483, U.S. Ser. No. 08/963,873 filed Nov. 4, 1997, U.S. Pat. No. 6,149,871, U.S. Pat. No. 6,309,362, WO 99/07823; U.S. Ser. No. 09/050,010 filed Mar. 30, 1998; WO 99/10723; U.S. Pat. No. 6,296,764 and WO 99/23468. The fixative solution of Example 1 exhibits rapid penetration of tissues with minimal amounts of artifacts; staining of the thus fixed tissues displays excellent histologic and cytologic detail.

Example 2

Cytology Preparation

1. Specimen collection containers are half-filled with the fixative composition of the instant invention. A specimen containing cells is placed into the container with the fixative composition.

2. The cytology specimen is mixed vigorously with the fixative composition to blend the specimen thoroughly with fixative.

3. If the cells of the cytology specimen are not dispersed, the specimen may be homogenized. Homogenization may be performed using a mechanical fin rotated at approximately 2,000 to 4,000 revolutions per minute (RPM), preferably at approximately 3,000 RPM. The fin at the bottom of the MonoGen™ Monoprep G performs this function. Alternatively, a blender may be used at high speed for 5 to 10 seconds or less. If flecks and fine threads are visible in the specimen, it may be returned to the blender for an additional 10 to 15 seconds. Avoid excessive blending 4. The cells should be permitted to fix for at least 15 minutes prior to further processing. Further processing includes methods well known to the art for the preparation of a cell monolayer and cell staining. A variety of cytology preparative devices may be used, such as those listed in Example 1.

Example 3

Cytology Preservation and Mucolytic Solution

The following fixative and mucolytic composition was produced: 40% alcohol (methanol and isopropanol); 2.2% acetone; 1.8% polyethylene glycol (PEG); 0.7% formaldehyde; 1% glycerol; 0.02% Nonidet P40; and 54% Tris Buffer (pH 7.4–7.8). All amounts are approximate percentages by volume. DTT is added in the range of 0.2–0.5% by grams. This solution is referred to as MonoLex™. The MonoLex™ solution is added to the specimen in a ratio of 1:1. The specimen and mucolytic fixative solution are votexes for approximately 1 minute, then incubated for approximately 30 minutes before being vortexed again for approximately 1 minute. Further processing includes methods well known to the art for the preparation of a particulate monolayer and cell staining. A variety of cytology preparative devices may be used, such as those listed in Example 1.

Example 4

Since cellular detail is dependent on fixation, it is preferred that cells be fixed either immediately after being deposited on the slide, such as for a cervical specimen, or prior to preparation of the cell monolayer. Too long a delay between preparation and fixation may expose the cells to drying, which may be detrimental to the cellular structure. Moreover, air drying artifacts can adversely affect the subsequent staining results. An exception is when the cells are stained with Wright-Giemsa Staiu, where air drying is used as the fixation step.

In an another embodiment of the present invention, the monolayer of cells may be fixed directly on the collection site. This may be carried out by first depositing a monolayer of cells on the collection site of the cytology collection apparatus as described above and subsequently passing a solution containing a fixative, such as alcohol or acetone, through the cytology collection apparatus.

Included within the scope of the present invention is the production of multiple specimens from a single patient sample. Additional slides for other stain applications can be easily prepared. Human papilloma virus testing, for example, by newer methods such as immunocytochemistry or in-situ hybridization can be performed on the additional slides. As oncogene products or other immunocytochemical tests are developed, more slides may be necessary. The different fixations that these tests may need can easily be incorporated into the procedure since the invention does not require the slides to be fixed in only one way.

This same slide preparation procedure can be used for virtually all forms of cytology. Furthermore, the use of completely contained disposable components addresses biohazard concerns. Ultimately, the enhanced presentation of cells, yielding improved cytologic interpretation, may expand the role of cytology by providing more consistent and reliable patient diagnosis.

In describing the invention, reference has been made to a preferred embodiment and illustrative advantages of the invention. Those skilled in the art, however, and familiar with the instant disclosure of the subject invention, may recognize that numerous other modifications, variations, and adaptations may be made without departing from the scope of the invention as defined in the claims.

What is claimed is:

1. A cytological and histological fixative composition comprising an aldehyde crosslinker at a concentration of about 0.2 to 4.0% by volume, a polyol at a concentration of about 0.5 to 2.0% by volume, a detergent at a concentration of about 0.01 to 0.05% by volume, a mixture of alcohols at a concentration of about 35 to about 45% by volume, acetone at a concentration of about 2.0 to 3.0% by volume, polyethylene glycol at a concentration of about 1.0 to 3.0% by volume and a buffer.

2. The composition of claim 1 wherein said aldehyde is $C_1$–$C_6$ alkanal or a $C_1$–$C_8$ alkylene dialdehyde.

3. The composition of claim 2 wherein said aldehyde is selected from the group consisting of glutaraldehyde, formaldehyde, paraformaldehyde, acetaldehyde, propionaldehyde, and butyraldehyde.

4. The composition of claim 1 wherein said polyol is selected from the group consisting of ethylene glycol, propylene glycol, glycerol, sorbitol, and mannitol.

5. The composition of claim 1 wherein said detergent is a non-ionic detergent.

6. The composition of claim 5 wherein said non-ionic detergent is selected from the group consisting of a polyethylene glycol, an ethoxylated sorbitan tristearate, an ethoxylated sorbitan monooleate and an ethoxylated sorbitan trioleate.

7. The composition of claim 1 wherein said buffer maintains the composition at a pH between about 4 and about 7.

8. The composition of claim 1 wherein said buffer is selected from the group consisting of Tris and phosphate buffered saline.

9. The composition of claim 1 further comprising a nucleoprotein precipitator or a hemolytic agent.

10. The composition of claim 9 wherein said nucleoprotein precipitator or hemolytic agent is acetic acid.

11. The composition of claim 1 further comprising an osmolarity maintainer.

12. The composition of claim 11, wherein said osmolarity maintainer is selected from the group consisting of dextrose and sodium chloride.

13. The composition of claim 1, wherein the mixture of alcohols comprises methanol and isopropanol.

14. The composition of claim 13, wherein the concentration of methanol is about 30% by volume and the concentration of isopropanol is about 10% by volume.

15. The composition of claim 1, further including a mucolytic agent.

16. The composition of claim 15 wherein said mucolytic agent is dithiothreitol or acetylcysteine.

17. The composition of claim 1, wherein the mixture of alcohols comprises ethanol.

* * * * *

UNITED STATES PATENT AND TRADEMARK OFFICE
CERTIFICATE OF CORRECTION

PATENT NO.      : 6,531,317 B2
DATED           : March 11, 2003
INVENTOR(S)     : Raouf A. Guirguis et al.

It is certified that error appears in the above-identified patent and that said Letters Patent is hereby corrected as shown below:

<u>Title page,</u>
Item [54], Title, delete "FIXATURE" and insert -- FIXATIVE --.
Item [75], Inventors, delete "Mariamena" and insert -- Mariana --.

Signed and Sealed this

Sixteenth Day of September, 2003

JAMES E. ROGAN
*Director of the United States Patent and Trademark Office*